United States Patent
Kosaka et al.

(10) Patent No.: US 12,139,444 B2
(45) Date of Patent: Nov. 12, 2024

(54) METHOD FOR MANUFACTURING HYDROCARBON COMPOUND FROM CARBON DIOXIDE AT CONCENTRATIONS INCLUDING LOW CONCENTRATION RANGE

(71) Applicant: National Institute of Advanced Industrial Science and Technology, Tokyo (JP)

(72) Inventors: Fumihiko Kosaka, Tsukuba (JP); Koji Kuramoto, Tsukuba (JP); Takehisa Mochizuki, Tsukuba (JP); Yanyong Liu, Tsukuba (JP); Shih-Yuan Chen, Tsukuba (JP); Hideyuki Takagi, Tsukuba (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days.

(21) Appl. No.: 18/019,490

(22) PCT Filed: Jul. 14, 2021

(86) PCT No.: PCT/JP2021/026401
§ 371 (c)(1),
(2) Date: Feb. 3, 2023

(87) PCT Pub. No.: WO2022/030203
PCT Pub. Date: Feb. 10, 2022

(65) Prior Publication Data
US 2023/0295059 A1  Sep. 21, 2023

(30) Foreign Application Priority Data
Aug. 6, 2020 (JP) ................. 2020-134131

(51) Int. Cl.
*C07C 1/12* (2006.01)
(52) U.S. Cl.
CPC .......... *C07C 1/12* (2013.01); *C07C 2523/755* (2013.01)
(58) Field of Classification Search
CPC . C07C 1/12; C07C 2523/755; C07C 2523/46; C07C 2523/58; C07C 2523/74;
(Continued)

(56) References Cited

U.S. PATENT DOCUMENTS

2016/0176775 A1   6/2016   Gruetzner et al.

FOREIGN PATENT DOCUMENTS

| CN | 109453782 A * | 3/2019 |
| JP | 2016-117726 A | 6/2016 |

(Continued)

OTHER PUBLICATIONS

International Search Report and Written Opinion mailed on Sep. 7, 2021, received for PCT Application PCT/JP2021/026401, filed on Jul. 14, 2021, 10 pages including English Translation.
(Continued)

*Primary Examiner* — Thuan D Dang
(74) *Attorney, Agent, or Firm* — XSENSUS LLP (57) ABSTRACT

A method for manufacturing a hydrocarbon compound from carbon dioxide, said method including: (a) a step of preparing an absorption-conversion catalyst that includes an oxide carrier, a first component supported on the oxide carrier and including at least one type of metal selected from the group consisting of alkali metals and alkaline earth metals, and a second component supported on the oxide carrier and including at least one type of metal selected from the group consisting of Ni, Fe, Co, Cu, and Ru; (b) a step of bringing the absorption-conversion catalyst and a carbon dioxide-including gas into contact under higher pressure than atmo-
(Continued)

spheric pressure, and causing the carbon dioxide to be stored in the absorption-conversion catalyst; and (c) a step of bringing the absorption-conversion catalyst that has the carbon dioxide stored therein and a reducing gas into contact under higher pressure than atmospheric pressure, and obtaining the hydrocarbon compound.

12 Claims, 7 Drawing Sheets

(58) Field of Classification Search
CPC . B01J 21/04; B01J 23/462; B01J 23/58; B01J 23/74; B01J 23/78
See application file for complete search history.

(56) References Cited

FOREIGN PATENT DOCUMENTS

| JP | 2018-135283 A | 8/2018 |
|---|---|---|
| JP | 2019-123678 A | 7/2019 |
| JP | 2019-151877 A | 9/2019 |
| JP | 2019-188353 A | 10/2019 |
| JP | 2020100597 A * | 7/2020 |

OTHER PUBLICATIONS

Nanase et al., "Development of K-based carrier particles for carbon dioxide utilization in carbonate looping", Proceeding of SCEJ 85th Annual Meeting (2020), PA162.

Wang et al., "Parametric, cyclic aging and characterization studies for CO2 capture from flue gas and catalytic conversion to synthetic natural gas using a dual functional material (DFM)", Journal of CO2 Utilization, vol. 27, 2018, pp. 390-397.

Veselovskaya et al., "Catalytic methanation of carbon dioxide captured from ambient air", Energy, vol. 159, 2018, pp. 766-773.

Kosaka et al., "Enhanced Activity of Integrated CO2 Capture and Reduction to CH4 under Pressurized Conditions toward Atmospheric CO2 Utilization", ACS Sustainable Chemistry Engineering., vol. 9, No. 9, Feb. 25, 2021, pp. 3452-3463.

* cited by examiner

METHOD FOR MANUFACTURING HYDROCARBON COMPOUND FROM CARBON DIOXIDE AT CONCENTRATIONS INCLUDING LOW CONCENTRATION RANGE

CROSS-REFERENCE TO RELATED APPLICATIONS

The present application is based on PCT filing PCT/JP2021/026401, filed Jul. 14, 2021, which claims priority to JP 2020-134131, filed Aug. 6, 2020, the entire contents of each are incorporated herein by reference.

TECHNICAL FIELD

The present invention relates to a method for producing a hydrocarbon compound from carbon dioxide ($CO_2$). More particularly, the present invention relates to a method for producing a hydrocarbon compound from $CO_2$ at concentrations including a low concentration range.

BACKGROUND ART

Conventionally, carbon recycling for absorbing $CO_2$ intensively generated from power plants, steel mills, chemical plants and the like and converting it to methane has been investigated. A method using a two-stage process is known, as an existing means, in which a low concentration of $CO_2$ contained in exhaust gas is separated and captured by a method such as amine absorption or membrane separation to concentrate it to a high concentration, and a hydrocarbon is synthesized by the catalyzed reaction of the highly concentrated $CO_2$ obtained by this concentration.

Further, Patent Document 1 discloses, as an example of a methanation catalyst that performs $CO_2$ absorption and conversion, a material in which: a $CO_2$ capture component selected from the group consisting of an alkali metal compound (Li, Na, K, Rb, Cs or the like) and an alkaline earth metal compound (Mg, Ca, Sr, Ba or the like); a methanation catalyst component selected from the group consisting of Ru, Ni and Co; and Si; are supported on an oxide support (such as an alumina support or a titania support). Patent document 1 examines the composition of the catalyst for efficiently carrying out the methanation of $CO_2$ even in cases where a raw material gas contains $O_2$ along with $CO_2$.

Non-patent Document 1 discloses $Ni/K_2CO_3/MgO$ and $Ni/K_2CO_3/ZrO_2$, as $CO_2$ absorption-conversion carrier particles (from 150 to 300 μm) capable of absorbing and converting $CO_2$ with a single material.

Non-patent Document 2 discloses a dual-functional material (DFM) capable of absorbing and converting $CO_2$ with a single material, and a DFM in which a $CO_2$ capture component (such as $Na_2O$) and a methanation catalyst component (such as Ru) are supported on $Al_2O_3$ (alumina) is described therein.

Non-patent Document 3 describes the direct air capture (DAC) of $CO_2$ contained in the atmosphere. First, $K_2CO_3/Al_2O_3$ in an absorption vessel is allowed to absorb $CO_2$ in the atmosphere, and then a high concentration of $CO_2$ accumulated in the absorption vessel is introduced into another reaction vessel in which an $Ru/Al_2O_3$ catalyst is kept, to perform methanation.

CITATION LIST

Patent Document

Patent Document 1 Japanese Patent Application Publication No. 2019-188353

Non-Patent Document

Non-patent Document 1 Koki Nanase et al., Proceeding of SCEJ 85th Annual Meeting (2020), PA162
Non-patent Document 2 S. Wang et al., J. of $CO_2$ utilization, Vol. 27, (2018), pp. 390 to 397
Non-patent Document 3 J. V. Veselovskaya et al., Energy, Vol. 159, (2018), pp. 766 to 773

SUMMARY OF INVENTION

Technical Problem

In view of the above-mentioned circumstances, an object of the present invention is to provide a means for directly capturing $CO_2$ at concentrations including a low concentration range by a catalyst itself, without having to perform a $CO_2$ separation operation such as amine absorption or membrane separation, and converting the captured $CO_2$ to a hydrocarbon compound.

Solution to Problem

The present inventors and others have conducted intensive studies to solve the above-mentioned problems.

As a result, the inventors and others have found out that it is possible to efficiency produce a hydrocarbon compound from $CO_2$ at concentrations including a low concentration range, by a method wherein an absorption-conversion catalyst in which a first component such as an alkali metal or an alkaline earth metal and a second component such as Ni, Fe, Co, Cu or Ru are supported on an oxide support is used, and the catalyst is brought into contact with $CO_2$ at a pressure higher than the atmospheric pressure, to produce a hydrocarbon compound.

Advantageous Effects of Invention

According to one embodiment, it is possible to directly capture $CO_2$ at concentrations including a low concentration range without having to perform separation and capture thereof, and to convert the captured $CO_2$ to a hydrocarbon compound at a high efficiency.

BRIEF DESCRIPTION OF THE DRAWINGS

FIGS. 2A to 2D show the graphs of the measured results of the integrated $CO_2$ capture and conversion to $CH_4$ using bifunctional catalysts at 450° C. and under the atmospheric pressure, as compared to that of a catalyst $Ni/Al_2O_3$. FIG. 2A shows the results using $Ni/Al_2O_3$; FIG. 2B shows the results using $Ni/Na-Al_2O_3$;
FIG. 2C shows the results using $Ni/K-Al_2O_3$; and FIG. 2D shows the results using $Ni/Ca-Al_2O_3$. The $CO_2$, $CH_4$ and CO concentrations are shown in each graph. Total flow rate: 500 mL/min, pressure: 1 atm. 5% $CO_2$, $N_2$ and $H_2$ were each supplied for 300 seconds, sequentially.

FIGS. 4A to 4B show the graphs of the $CO_2$ capture and conversion performances at various pressures (from 1 to 9 atm).

FIGS. 5A to 5H show the graphs of the concentrations of the reaction products in the integrated dilute $CO_2$ capture and conversion using the Ni/Na-$Al_2O_3$ catalyst. FIGS. 5A and 5B show the results at 1 atm, and FIGS. 5C and 5D show the results at 9 atm. The $CO_2$ supply durations were 10, 30 and 100 minutes. Total flow rate: 500 mL/min.

FIGS. 6A to 6E show the graphs of the $CO_2$ capture and conversion performances using Ni/Na-$Al_2O_3$ in the integrated dilute $CO_2$ capture and conversion cycle, at 1 atm and at 9 atm.

DESCRIPTION OF EMBODIMENTS

Embodiments of the present invention will be described below.

<Method for Producing Hydrocarbon Compound from Carbon Dioxide>

An embodiment of the present invention relates to a method for producing a hydrocarbon compound from carbon dioxide, the method including the steps of:

(a) providing an absorption-conversion catalyst including:
an oxide support;
a first component supported on the oxide support and including at least one selected from the group consisting of an alkali metal and an alkaline earth metal; and
a second component supported on the oxide support and including at least one selected from the group consisting of Ni, Fe, Co, Cu and Ru;

(b) bringing the absorption-conversion catalyst into contact with a gas containing carbon dioxide at a pressure higher than an atmospheric pressure, to allow the absorption-conversion catalyst to capture carbon dioxide; and (c) bringing the absorption-conversion catalyst in which carbon dioxide is captured into contact with a reducing gas at a pressure higher than an atmospheric pressure, to obtain a hydrocarbon compound.

As described above, techniques for the capture and reuse of a high concentration of carbon dioxide have been investigated. However, a sufficient investigation has not been done for improving the efficiency of the techniques for the capture and reuse of a low concentration of carbon dioxide. The present embodiment has been made based on the finding by the present inventors and others that, by performing reactions at a pressure higher than the atmospheric pressure in the step of allowing the absorption-conversion catalyst to capture carbon dioxide and in the step of converting (hereinafter, also referred to as "hydrocarbonation") carbon dioxide to a hydrocarbon, it is possible to improve the carbon dioxide capture performance of the absorption-conversion catalyst and the carbon dioxide hydrocarbonation performance of the absorption-conversion catalyst. Thus, the present embodiment provides a means for capturing low-concentration $CO_2$ from a gas containing carbon dioxide at concentrations including a low concentration range, without having to separate and concentrate the same, and efficiently producing a hydrocarbon compound. That is, the present embodiment can be expected to be used for the removal of carbon dioxide from the atmosphere containing a low concentration of $CO_2$, and the like.

In the step (a), an absorption-conversion catalyst comprising: an oxide support; a first component supported on the oxide support and comprising at least one selected from the group consisting of an alkali metal and an alkaline earth metal; and a second component supported on the oxide support and comprising at least one selected from the group consisting of Ni, Fe, Co, Cu and Ru; is provided.

The term "absorption-conversion catalyst" as used herein refers to a catalyst having an ability to absorb carbon dioxide under predetermined conditions and an ability to convert carbon dioxide to a hydrocarbon compound using a reducing gas.

The above-described absorption-conversion catalyst comprises: an oxide support; a first component supported on the oxide support and comprising at least one selected from the group consisting of an alkali metal compound and an alkaline earth metal compound; and a second component supported on the oxide support and comprising at least one selected from the group consisting of Ni, Fe, Co, Cu and Ru.

The oxide support in the absorption-conversion catalyst is not particularly limited as long as it is used as a catalyst support. From the viewpoint of its high activity, however, the oxide support is preferably an alumina support, a silica support, a titania support, a zirconia support, a ceria support, a magnesia support or the like, and more preferably an alumina support. These oxide supports may be used singly, or in combination of two or more kinds thereof.

The absorption-conversion catalyst preferably has, but not particularly limited to, an average particle size (median diameter, D50) of from 0.1 to 500 μm, more preferably from 1 to 300 μm, and particularly preferably from 50 to 200 μm, from the viewpoint of usability. The absorption-conversion catalyst preferably has a specific surface area of from 10 to 2,000 m²/g, more preferably from 20 to 1,000 m²/g, and particularly preferably from 30 to 500 m²/g, but not particularly limited thereto, as well. The average particle size of the absorption-conversion catalyst can be measured, for example, by the dynamic light scattering method, the small-angle X-ray scattering method, the laser diffraction method or the like. The specific surface area of the absorption-conversion catalyst can be measured, for example, by the gas absorption method, the permeation method or the like.

The first component comprising at least one selected from the group consisting of an alkali metal and an alkaline earth metal, is a carbon dioxide capture component.

In the above-described absorption-conversion catalyst, the carbon dioxide capture component is supported on the oxide support. The carbon dioxide capture component selectively captures carbon dioxide, and the captured carbon dioxide is allowed to react with a reducing gas in the presence of a catalyst component for converting carbon dioxide to a hydrocarbon (hereinafter, referred to as "hydrocarbonation catalyst component"), to produce a hydrocarbon compound from carbon dioxide.

Examples of the carbon dioxide capture component include an alkali metal and an alkaline earth metal. Examples of the alkali metal include Li, Na, K, Rb and Cs. Among these, Na and K are preferred, and Na is particularly preferred. Examples of the alkaline earth metal include Mg, Ca, Sr and Ba. Among these, Ca is preferred from the viewpoint of durability. These carbon dioxide capture components may be used singly, or in combination of two or more kinds thereof.

When the amount of the carbon dioxide capture component to be supported is too small, the carbon dioxide capture performance of the absorption-conversion catalyst is decreased, and fails to efficiently reduce carbon dioxide, thereby resulting in a decrease in the production efficiency of producing a hydrocarbon compound from carbon dioxide. When the amount of the carbon dioxide capture component to be supported is too large, on the other hand, the coarsening of the carbon dioxide capture component, the pore clogging of the oxide support and the like occur, thereby resulting in a decrease in the carbon dioxide capture performance and the production efficiency of the hydrocarbon compound. From such points of view, the amount of the carbon dioxide capture component to be supported is preferably from 0.1 to 40 parts by mass, more preferably from 1 to 30 parts by mass, and particularly preferably from 5 to 20 parts by mass, with respect to 100 parts by mass of the oxide support.

The second component comprising at least one selected from the group consisting of Ni, Fe, Co, Cu and Ru is a hydrocarbonation catalyst component.

In the above-described absorption-conversion catalyst, at least one or a combination of a plurality of hydrocarbonation catalyst components selected from the group consisting of Ni, Fe, Co, Cu and Ru, is/are supported on the oxide support. In the presence of the hydrocarbonation catalyst component, the carbon dioxide captured in the above-described carbon dioxide capture component is allowed to react with a reducing gas, to produce a hydrocarbon compound from carbon dioxide.

Examples of the hydrocarbonation catalyst component include Ni, Fe, Co, Cu and Ru. Among these, Ni is preferred.

When the amount of the hydrocarbonation catalyst component to be supported is too small, the reduction reaction of carbon dioxide is not sufficiently facilitated, thereby resulting in a decrease in the production efficiency of producing a hydrocarbon from carbon dioxide. When the amount of the hydrocarbonation catalyst component to be supported is too large, on the other hand, the coarsening of the hydrocarbonation catalyst component, the pore clogging of the oxide support and the like occur, thereby resulting in a decrease in the carbon dioxide capture performance and methane production efficiency. From such points of view, the amount of the hydrocarbonation catalyst component to be supported is preferably from 0.1 to 40 parts by mass, more preferably from 1 to 30 parts by mass and particularly preferably from 5 to 20 parts by mass, with respect to 100 parts by mass of the oxide support.

The absorption-conversion catalyst described above can be produced based on a known method for producing an absorption-conversion catalyst. For example, the absorption-conversion catalyst can be produced by the method described in the Examples of the present specification.

In the step (b), the absorption-conversion catalyst is brought into contact with a gas containing carbon dioxide at a pressure higher than an atmospheric pressure, to allow the absorption-conversion catalyst to capture carbon dioxide. In the production method according to the present embodiment, the carbon dioxide capture performance of the absorption-conversion catalyst and the carbon dioxide hydrocarbonation performance of the absorption-conversion catalyst can be improved, by performing the reactions at a pressure higher than the atmospheric pressure. Therefore, it is possible to perform the conversion to a hydrocarbon compound also from a gas containing a low concentration of carbon dioxide.

The method for adjusting the pressure of the atmosphere in which the absorption-conversion catalyst is allowed to capture carbon dioxide to a pressure higher than the atmospheric pressure is not particularly limited, as long as such a high pressure can be achieved. For example, the method may be one in which a gas containing carbon dioxide, as a raw material, is pressurized and introduced into a reactor, or the like.

The pressure of the atmosphere in which the absorption-conversion catalyst is allowed to capture carbon dioxide is preferably more than 1 and not more than 9 atm, more preferably from 1.5 to 9 atm, still more preferably from 3 to 9 atm, and particularly preferably from 6 to 9 atm, from the viewpoints of inhibiting the degradation of the catalyst and obtaining a high carbon dioxide capture efficiency.

The temperature of the atmosphere in which the absorption-conversion catalyst is allowed to capture carbon dioxide can be adjusted as appropriate, depending on the pressure and the like of the atmosphere. However, the temperature is preferably from room temperature to 600° C., from the viewpoints of inhibiting the condensation of moisture to the catalyst and the oxidation of the hydrocarbonation catalyst component.

The period of time during which the absorption-conversion catalyst is allowed to capture carbon dioxide can be adjusted as appropriate, depending on the pressure, the temperature, the carbon dioxide concentration and the like, of the atmosphere.

The concentration of carbon dioxide in the gas as the raw material in the production method according to the present embodiment, is not particularly limited. As described above, it is possible to perform the conversion to a hydrocarbon compound also from a gas containing a low concentration of carbon dioxide. Specifically, the conversion to a hydrocarbon compound can be performed also from the air, which is a gas that usually contains carbon dioxide at a low concentration of about 300 ppm. Therefore, it is preferred that the concentration of carbon dioxide in the gas as the raw material be, for example, from 0.01 to 5 vol % (from 100 to 50,000 ppm), more preferably from 0.03 to 5 vol % (from 300 to 50,000 ppm), and still more preferably from 0.04 to 3 vol % (from 400 to 30,000 ppm), and yet still more preferably from 0.1 to 1 vol % (from 1,000 to 10,000 ppm).

The reducing gas is not particularly limited as long as carbon dioxide can be converted to a hydrocarbon compound. However, pure hydrogen gas or a hydrogen-containing gas is preferred. It is also possible to use a hydrogen gas obtained by water electrolysis using an energy-saving power generation system, as the reducing gas. Another gas(es) to be contained in the hydrogen-containing gas is/are not particularly limited as long as the reduction reaction of carbon dioxide is not inhibited. However, an inert gas such as a helium gas, a nitrogen gas and/or the like is/are preferred. The concentration of hydrogen in the hydrogen-containing gas is preferably 5 vol % or more, and more preferably 10 vol % or more, from the viewpoint of improving the reduction efficiency.

In the step (c), the absorption-conversion catalyst in which carbon dioxide is captured is brought into contact with a reducing gas at a pressure higher than a atmospheric pressure, to obtain a hydrocarbon compound.

The method for adjusting the pressure of the atmosphere in which the captured carbon dioxide is allowed to react with a reducing gas to a pressure higher than the atmospheric pressure is not particularly limited as long as such a high can be achieved. For example, the method may be one in which a reducing gas is pressurized and introduced into a reactor, or the like.

The pressure of the atmosphere in which the captured carbon dioxide is allowed to react with a reducing gas is preferably more than 1 and not more than 9 atm, more preferably from 1.5 to 9, still more preferably from 3 to 9 atm, and particularly preferably from 6 to 9 atm, from the viewpoints of inhibiting the degradation of the catalyst and obtaining a high efficiency for producing a hydrocarbon compound.

The temperature of the atmosphere in which the captured carbon dioxide is allowed to react with a reducing gas can be adjusted as appropriate, depending on the pressure and the like of the atmosphere. However, the temperature is preferably from 150 to 700° C., and more preferably from 300 to 500° C., from the viewpoints of achieving an improvement in the production rate of the resulting hydrocarbon compound and the inhibition of carbon dioxide desorption during reduction, and obtaining a high efficiency for producing a hydrocarbon compound.

The period of time during which the captured carbon dioxide is allowed to react with a reducing gas can be adjusted as appropriate, depending on the pressure, the temperature, the carbon dioxide concentration and the like, of the atmosphere.

(Hydrocarbon Compound)

The hydrocarbon compound to be obtained in the step (c) is not particularly limited. Examples thereof include hydrocarbons having carbon number of 1 to 5 (such as methane, ethane, propane, n-butane, isobutane, n-pentane, isopentane, neopentane, ethylene and propylene). Among these, methane and ethane are preferred, and methane is more preferred. Further, examples of compounds to be obtained in the step (c), in addition to the hydrocarbon compound, include carbon monoxide (CO) and alcohols (such as methanol and ethanol).

In the production method according to the present embodiment, the synthesis ratio of the hydrocarbon compound, carbon monoxide (CO) and an alcohol can be adjusted, by adjusting the conditions in the production method based on the Examples to be described later and conventional methods.

<Apparatus for Carrying Out Production Method of Embodiment>

Another embodiment of the present invention relates to an apparatus for carrying out the production method according to the present embodiment, wherein the apparatus is a circulating fluidized bed type reactor, comprising:

a carbon dioxide capture reactor, a hydrocarbon compound synthesis reactor, and a catalyst circulation path connecting the carbon dioxide capture reactor and the hydrocarbon compound synthesis reactor.

The use of a circulating fluidized bed allows the catalyzed reaction of capturing and converting $CO_2$ to proceed continuously. Further, it is possible to allow the catalyzed reaction to proceed at a high flow rate, by using a scaled-up version of such a circulating fluidized bed.

Figure 1:
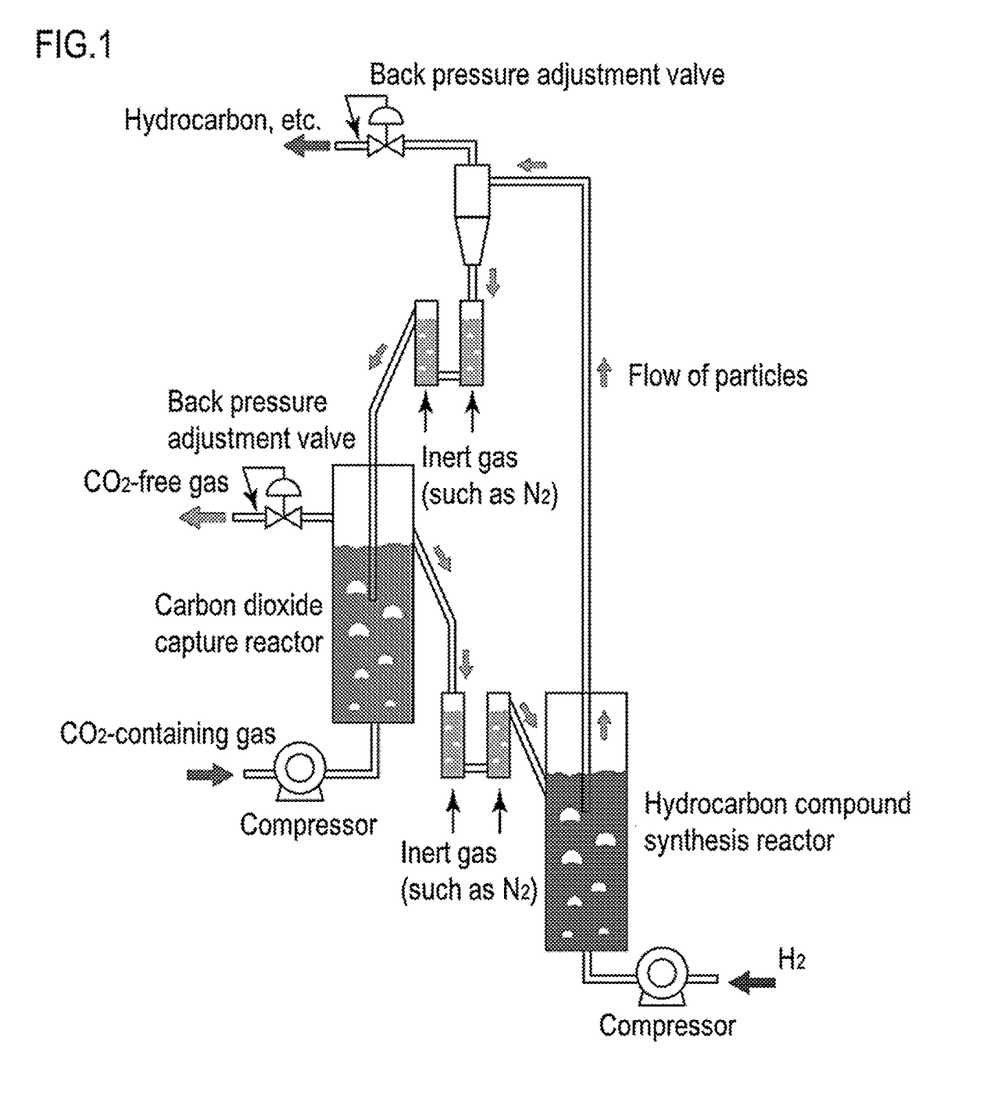
FIG. 1 is a schematic diagram illustrating an integrated $CO_2$ capture and conversion system according to an embodiment of the present invention.

FIG. 1 shows an apparatus according to the present embodiment.

The circulating fluidized bed type reactor shown in FIG. 1 comprises: a carbon dioxide capture reactor for capturing carbon dioxide, by bringing the absorption-conversion catalyst into contact with a gas containing carbon dioxide to allow the absorption-conversion catalyst to capture carbon dioxide; a hydrocarbon compound synthesis reactor for synthesizing a hydrocarbon compound, by bringing the absorption-conversion catalyst in which carbon dioxide is captured into contact with a reducing gas; and a catalyst circulation path provided so as to connect the carbon dioxide capture reactor and the hydrocarbon compound synthesis reactor, and for circulating the catalyst between the two reactors. The circulating fluidized bed in this apparatus is composed of a fluid medium at least a part of which is the absorption-conversion catalyst.

At the lower portion of a container filled with the carbon dioxide capture reactor, a gas delivery pipe for blowing a gas containing carbon dioxide into the container, and a compressor for pressurizing the gas to be introduced into the container are provided. Further, an introduction pipe extending from the catalyst circulation path and for introducing the catalyst into the container is provided at the upper portion of the container. On the side walls of the container, a gas discharge pipe for discharging the gas in the container and a back pressure adjustment valve for decompressing the gas to be discharged out of the container, as well as a discharge pipe extending to the catalyst circulation path and for discharging the catalyst from the container are provided.

In the carbon dioxide capture reactor, a gas containing carbon dioxide is blown thereinto through the gas delivery pipe to allow the circulating fluidized bed filled in the container to rise. During the above-described process, the circulating fluidized bed is stirred and mixed, and carbon dioxide is captured in the absorption-conversion catalyst.

The catalyst discharged from the container filled with the carbon dioxide capture reactor is supplied to a container filled with the hydrocarbon compound synthesis reactor, passing through the catalyst circulation path connecting the carbon dioxide capture reactor and the hydrocarbon compound synthesis reactor. A gas replacement unit in which the catalyst is brought into contact with an inert gas is provided in the catalyst circulation path.

At the lower portion of the container filled with the hydrocarbon compound synthesis reactor, a gas delivery pipe for blowing a reducing gas into the container, and a compressor for pressurizing the gas to be introduced into the container are provided. Further, a discharge pipe extending to the catalyst circulation path and for discharging the catalyst from the container is provided at the upper portion of the container. On the side wall of the container, an introduction pipe extending from the catalyst circulation path and for introducing the catalyst into the container is provided.

In the hydrocarbon compound synthesis reactor, a gas containing a reducing gas is blown thereinto through the gas delivery pipe to allow the circulating fluidized bed filled in the container to rise. During the above-described process, the circulating fluidized bed is stirred and mixed, the carbon dioxide captured in the absorption-conversion catalyst reacts with the reducing gas, and a hydrocarbon compound is synthesized from the carbon dioxide. At this time, the release of the carbon dioxide captured once in the catalyst is an endothermic reaction, which requires heating. In contrast, the synthesis of the hydrocarbon compound from the carbon dioxide with the reducing gas is an exothermic reaction. Thus, the exothermic reaction and the endothermic reaction proceed simultaneously in the absorption-conversion catalyst during this process, and therefore, the heating for releasing the captured carbon dioxide is supplemented completely or partially, thereby achieves energy saving.

The catalyst discharged from the container filled with the hydrocarbon compound synthesis reactor is supplied to a capture unit for capturing the catalyst and the like, passing through the catalyst circulation path. In the capture unit, the gas formed and the catalyst are separated, the gas formed is discharged through a discharge pipe, and the catalyst is returned to the carbon dioxide capture reactor through the catalyst circulation path. In the catalyst circulation path, a gas replacement unit in which the catalyst is brought into contact with an inert gas is provided, to separate the gas atmosphere in the carbon dioxide gas absorption reactor from that in the synthesis reactor.

EXAMPLES

The present invention will be described in a more specific detail with reference to Examples. However, the present invention is in no way limited to these Examples, as long as the gist of the invention is not deviated.

<Preparation of Ni/(Na, K or Ca)-$Al_2O_3$ Catalyst and Ni/$Al_2O_3$ Catalyst >

Gamma alumina ($\gamma$-$Al_2O_3$, sample cord: JRC-ALO-5) (particle size range: from 74 to 125 μm) provided by the Catalyst Society of Japan was used without processing. The $\gamma$-$Al_2O_3$ was impregnated with 50 mL of an aqueous solution containing an appropriate amount of an alkali metal carbonate or an alkaline earth metal nitrate, such as sodium carbonate ($Na_2(CO_3)$, manufactured by FUJIFILM Wako Pure Chemical Corporation), potassium carbonate ($K_2(CO_3)$, manufactured by FUJIFILM Wako Pure Chemical Corporation) or calcium carbonate ($Ca(NO_3)_2$, manufactured by FUJIFILM Wako Pure Chemical Corporation). Thereafter, the impregnated $\gamma$-$Al_2O_3$ was dried overnight at 110° C., and baked at 550° C. in the air for four hours, to obtain a Na-$\gamma$-$Al_2O_3$ support, a K-$\gamma$-$Al_2O_3$ support or a Ca-$\gamma$-$Al_2O_3$ support. The amount of the alkali metal carbonate or the alkaline earth metal carbonate to be added was maintained at 15% by mass with respect to the amount of $\gamma$-$Al_2O_3$. Subsequently, $Al_2O_3$, the Na-$\gamma$-$Al_2O_3$ support, the K-$\gamma$-$Al_2O_3$ support or the Ca-$\gamma$-$Al_2O_3$ support was impregnated with 50 ml of an aqueous solution of nickel nitrate ($Ni(NO_3)_2 \cdot 6H_2O$, manufactured by FUJIFILM Wako Pure Chemical Corporation) by the same procedure and under the same drying and baking conditions. As a result, Ni/$Al_2O_3$,1 Ni/Na-$Al_2O_3$, Ni/K-$Al_2O_3$ or Ni/Ca-$Al_2O_3$ was obtained. The amount of Ni to be added was maintained at 10% by mass with respect to the amount of each support.

<Integrated $CO_2$ Capture and Conversion to Methane >

Experiments were carried out based on the following methods.

One gram of Ni/$Al_2O_3$, Ni-Na/$Al_2O_3$, Ni/K-$Al_2O_3$ or Ni/Ca-$Al_2O_3$ catalyst was placed in a SUS pipe in an electric furnace. Before the measurement, each catalyst was pretreated at 500° C. in a $H_2$ atmosphere for one hour. To measure the integrated $CO_2$ capture and conversion, x % $CO_2$ (x=from 0.01 to 5) and $H_2$ were sequentially supplied into a reactor for y minutes (y=from 5 to 100) and 5 minutes, respectively. $N_2$ was also supplied for 5 minutes as a purge gas to be used between $CO_2$ and $H_2$ streams. Each measurement was carried out at 450° C., a pressure of from 1 to 9 atm and a rate of 500 mL/min. The outlet gas was monitored using a non-dispersive infrared (NDIR) gas analyzer (VA-5000, manufactured by HORIBA, Ltd.) and a BELMass mass spectrometer. The concentrations of $CH_4$, $CO_2$ and CO in the outlet gas were measured using the NDIR gas analyzer. The reaction temperature was monitored by inserting a thermocouple into the catalyst.

FIGS. 2A to 2D show the measured results of the $CO_2$ capture and conversion experiments at 450° C. and under the atmospheric pressure (1 atm), using various catalysts: Ni/$Al_2O_3$(Experiment 1), Ni/K-$Al_2O_3$(Experiment 2), Ni/Ca-$Al_2O_3$ (Experiment 3) and Ni/Na-$Al_2O_3$(Experiment 4). The compositions of the respective catalysts and the measured results using the same are shown in Table 1.

TABLE 1

| | Supported amount with respect to 100 parts by mass of oxide carrier [part by mass] | | | | Concentration of $CO_2$ supplied | Reaction pressure | Amount of $CH_4$ formed |
|---|---|---|---|---|---|---|---|
| | Ni | $Na_2CO_3$ | $K_2CO_3$ | $CaCO_3$ | [%] | [atm] | [μmol g-cart$^{-1}$] |
| Experiment 1 | 11 | 0 | 0 | 0 | 5 | 1 | 15 |
| Experiment 2 | 13 | 0 | 17.6 | 0 | 5 | 1 | 117 |
| Experiment 3 | 13 | 0 | 0 | 17.6 | 5 | 1 | 68 |
| Experiment 4 | 13 | 17.6 | 0 | 0 | 5 | 1 | 188 |
| Experiment 5 | 13 | 17.6 | 0 | 0 | 5 | 9 | 303 |
| Experiment 6 | 13 | 17.6 | 0 | 0 | 0.03 | 9 | 122 |
| Experiment 7 | 13 | 17.6 | 0 | 0 | 0.01 | 9 | 106 |

First, 5% $CO_2$ was supplied to the reactor to allow the catalyst to absorb $CO_2$. Thereafter, $N_2$ was purged into the gas supply line and to the $CO_2$ in the reactor. Finally, pure $H_2$ was supplied to the reactor, to convert the $CO_2$ absorbed in the catalyst to $CH_4$.

Figure 2A:
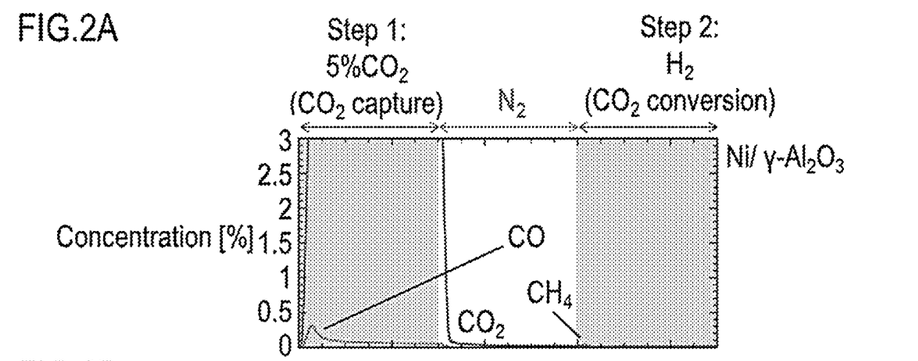
Figure 2B:
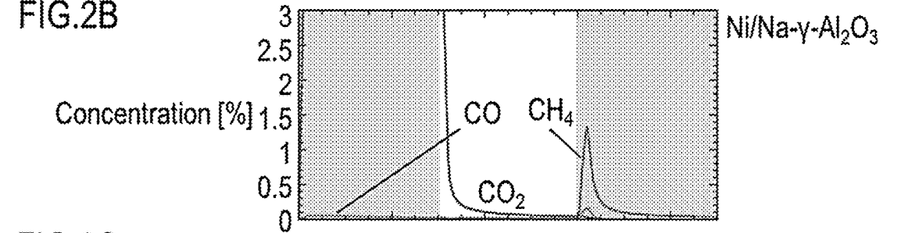
Figure 2C:
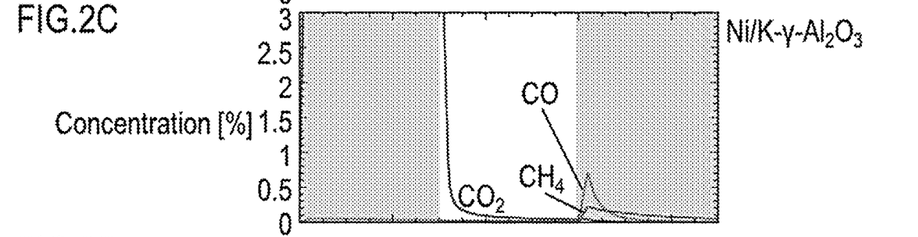
Figure 2D:
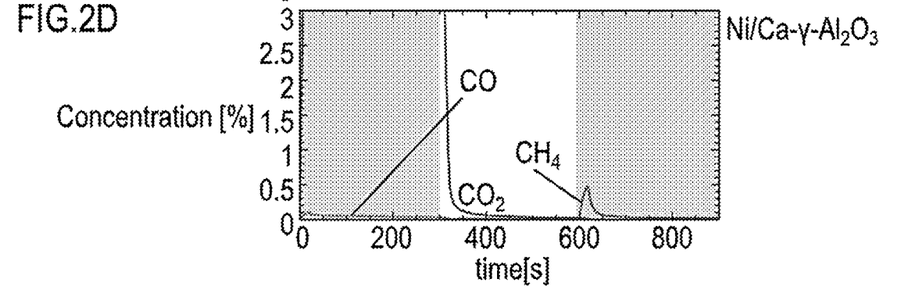
Figure 3A:
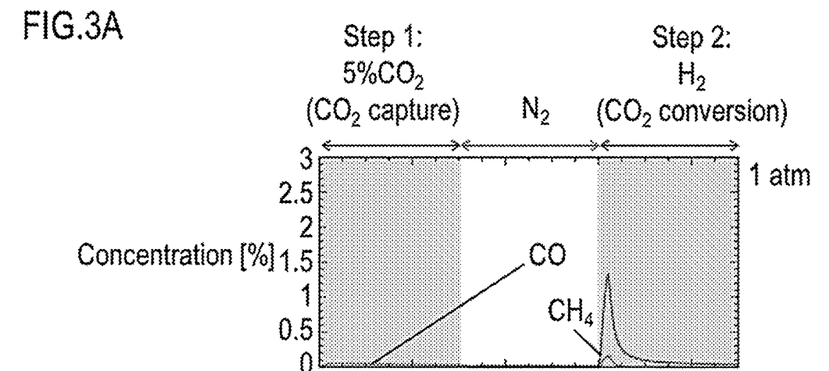
FIGS. 3A to 3D show the graphs of the concentrations of the reaction products in the integrated dilute $CO_2$ capture and conversion using the Ni/Na-$Al_2O_3$ catalyst at various pressures (from 1 to 9 atm). Total flow rate: 500 mL/min. 5% $CO_2$, $N_2$ and $H_2$ were each supplied for 300 seconds, sequentially.
Figure 3B:
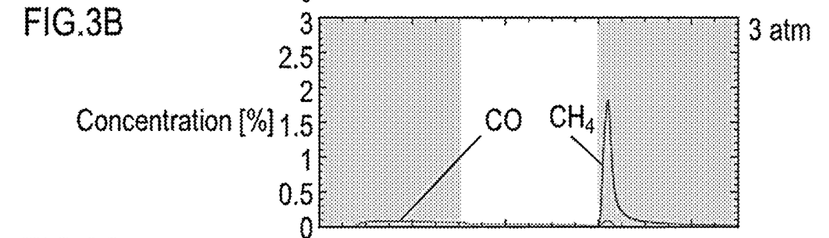
Figure 3C:
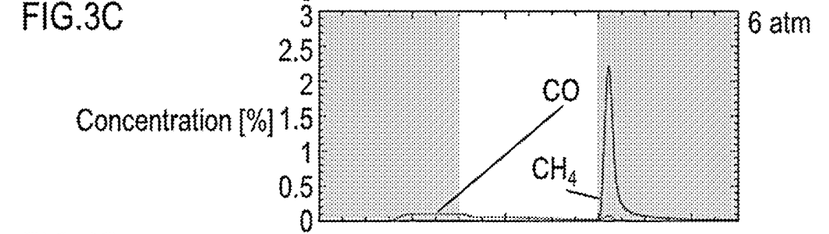
Figure 3D:
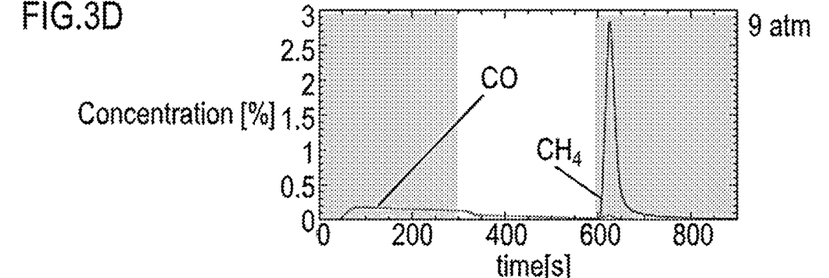

As shown in FIGS. 2A to 2D, Ni/Na-$Al_2O_3$ showed the highest activity in the experiments of the integrated $CO_2$ capture and conversion to $CH_4$ under the atmospheric pressure. Further, as shown in FIG. 2C, Ni/K-$Al_2O_3$ showed a higher efficiency in the conversion to carbon monoxide, CO, than to $CH_4$.

Further, the effects of pressurized conditions (from 1 to 9 atm) and $CO_2$ concentrations (5% and 100 ppm $CO_2$) on the performances of $CO_2$ capture and conversion to $CH_4$ were examined and studied.

FIGS. 3A to 3D show the measured results of the $CO_2$ capture and conversion experiments at 450° C. and at pressures of from 1 to 9 atm. The $CH_4$ formation increased significantly as the reaction pressure increases, and the peak $CH_4$ concentration at 9 atm was about twice that at 1 atm (Experiment 5). The $CH_4$ formation showed a sharp peak under pressurized conditions, namely, even at 9 atm, and the reaction of the absorbed $CO_2$ to $CH_4$ proceeded sufficiently rapidly.

Figure 4A:
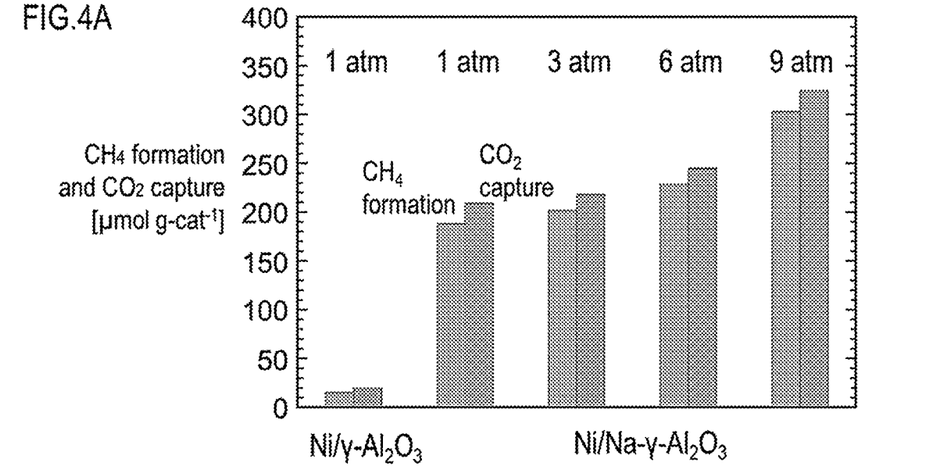
FIG. 4A shows the amounts of $CH_4$ formed and $CO_2$ captured, per mass of the catalyst (Ni/$Al_2O_3$ or Ni/Na-$Al_2O_3$)
Figure 4B:
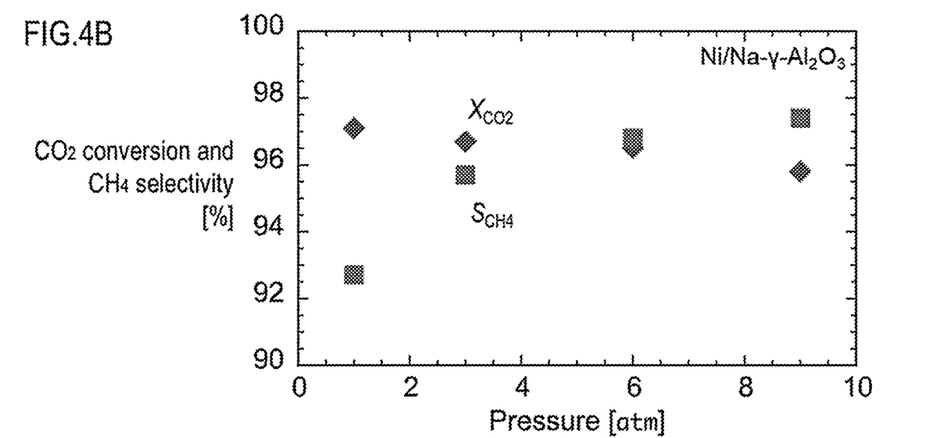
FIG. 4B shows the $CO_2$ conversion rate ($X_{CO2}$) and the $CH_4$ selectivity ($S_{CH4}$) during the integrated dilute $CO_2$ capture and conversion cycle.

FIG. 4A shows the amounts of $CH_4$ formed and $CO_2$ captured using $Ni/Al_2O_3$, or the $Ni/Na-Al_2O_3$ bifunctional catalyst, at various pressures. While the amounts of $CH_4$ formed and $CO_2$ captured using $Ni/Al_2O_3$ were extremely small, high amounts of $CH_4$ formed and $CO_2$ captured were observed with the use of the $Ni/Na-Al_2O_3$ bifunctional catalyst. Both the amounts of $CH_4$ formed and $CO_2$ captured continuously increased with an increase in the reaction pressure. FIG. 4B shows the $CO_2$ conversion ($X_{CO2}$) and $CH_4$ selectivity ($S_{CH4}$) using $Ni/Na-Al_2O_3$, corresponding to each reaction pressure. The amounts of $CO_2$ converted were almost the same between pressures of from 1 to 9 atm, and the $CH_4$ selectivity increased with an increase in the reaction pressure. These results suggest that the reaction pressure has positive effects on the $CO_2$ capture and conversion performances using a bifunctional catalyst such as $Ni/Na-Al_2O_3$.

The integrated capture and conversion of 5% $CO_2$ were investigated, as described above, and the application thereof to lower concentrations of $CO_2$ was further investigated. The effects of pressurized conditions on the direct conversion from a dilute $CO_2$, specifically, $CO_2$ at a concentration of 100 ppm or 300 ppm, to $CH_4$ were examined.

FIGS. 5A to 5H show the results of the direct conversion from 100 ppm (Experiment 6) or 300 ppm (Experiment 7) $CO_2$ to $CH_4$ using the $Ni/Na-Al_2O_3$ catalyst, at 1 atm or 9 atm, with $CO_2$ supply durations of from 10 to 100 minutes. FIGS. 5A to 5D each shows the results of performing one absorption-conversion sequence (consisting of $CO_2$ absorption, $N_2$ purge and $CH_4$ synthesis) three times sequentially, varying the supply duration of $CO_2$ in three stages (10 minutes, 30 minutes and 100 minutes). FIGS. 5E to 5H are graphs in which the ordinates of FIGS. 5A to 5D are enlarged.

Figure 5A:
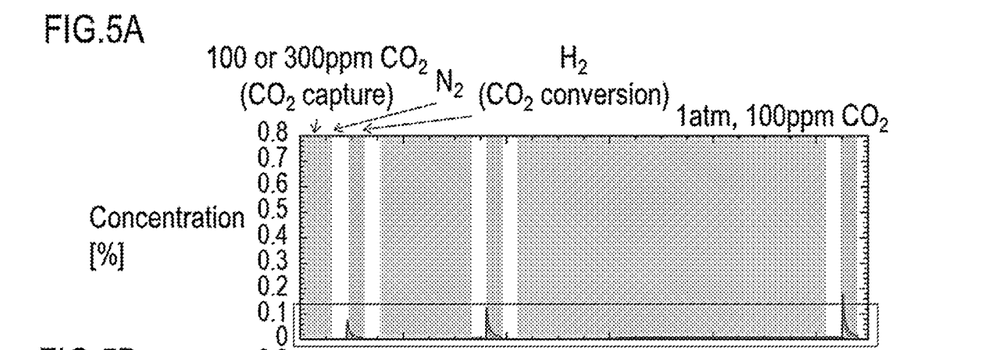
FIGS. 5A and 5C show the results for 100 ppm $CO_2$.
Figure 5B:
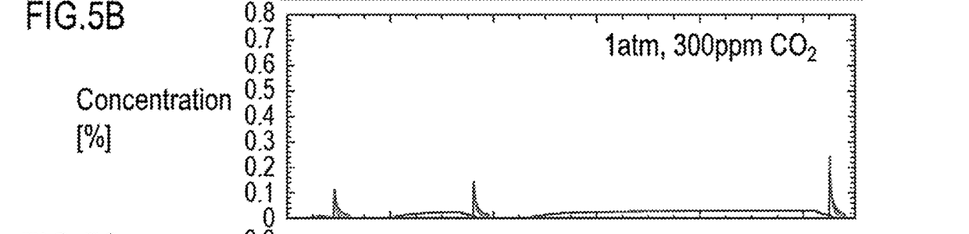
FIGS. 5B and 5D show the results for 300 ppm $CO_2$.
Figure 5C:
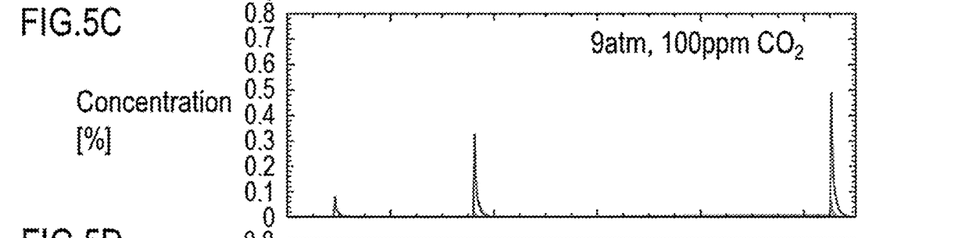
Figure 5D:
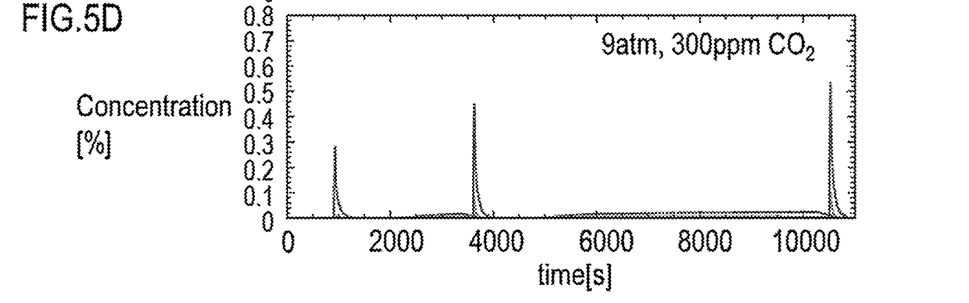
Figure 5E:
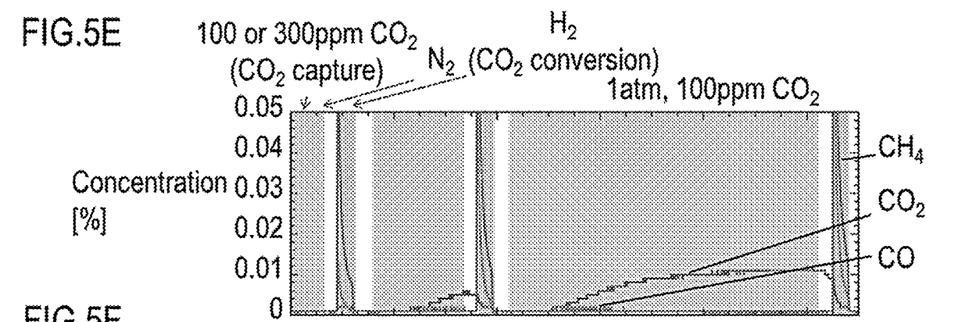
FIGS. 5E to 5H are enlarged views of FIGS. 5A to 5D.
Figure 5F:
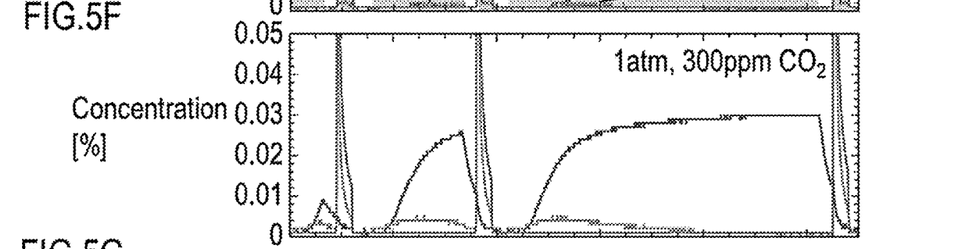
Figure 5G:
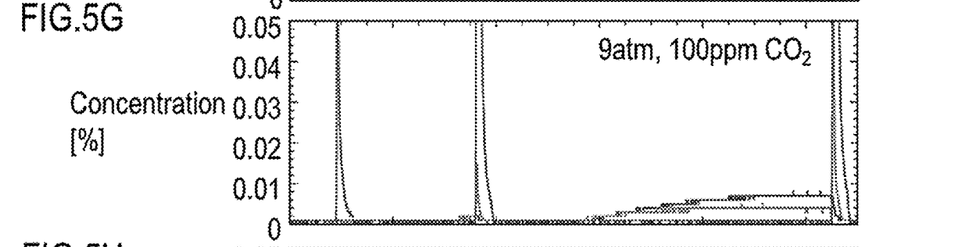
Figure 5H:
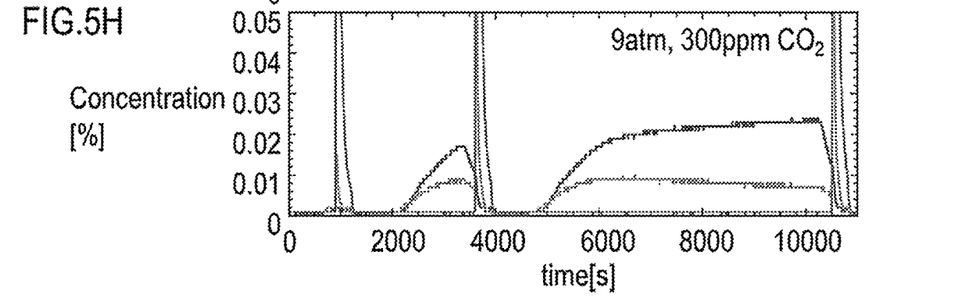

As shown in FIGS. 5E and 5G, in cases where 100 ppm $CO_2$ was supplied for 10 minutes, the $CO_2$ concentration is extremely low in the outlet gas, suggesting that most of the supplied $CO_2$ was absorbed by the catalyst. In cases where 100 ppm $CO_2$ was supplied for 30 minutes, in contrast, $CO_2$ was observed in the outlet gas at 1 atm, but barely observed at 9 atm, showing that most of $CO_2$ was s absorbed by the catalyst. These results show that the $CO_2$ absorption by the catalyst is increased by applying a pressure. In cases where 100 ppm $CO_2$ was supplied for 100 minutes, the $CH_4$ formation more than doubled when the pressure is increased from 1 atm to 9 atm. While the CO formation proceeded to about the same degree as the $CH_4$ formation at 1 atm, the CO formation was inhibited at 9 atm and a high $CH_4$ selectivity was achieved.

FIGS. 6A to 6E show the dependency of the $CH_4$ formation, the CO formation, the $CO_2$ absorption, the $CO_2$ conversion rate and the $CH_4$ selectivity (FIGS. 6A to 6E), per catalyst mass, on the $CO_2$ supply duration, at 1 atm and at 9 atm. FIGS. 6A to 6E are the summaries of the experimental results shown in FIGS. 5A and 5C, obtained by plotting the respective data acquired for $CO_2$ supply durations of 10 minutes, 30 minutes and 100 minutes.

Figure 6A:
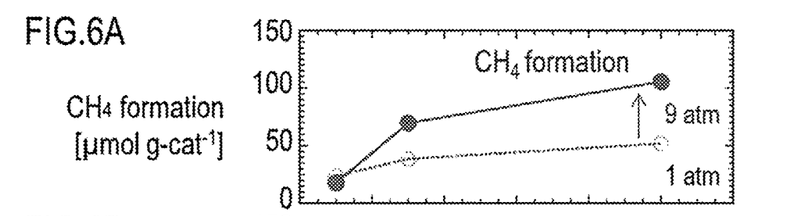
FIG. 6A shows the amount of $CH_4$ formed per catalyst mass.
Figure 6B:
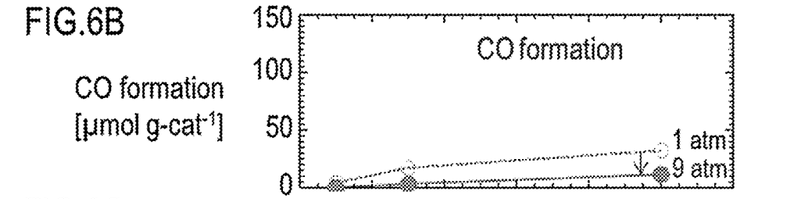
FIG. 6B shows the amount of CO formed.
Figure 6C:
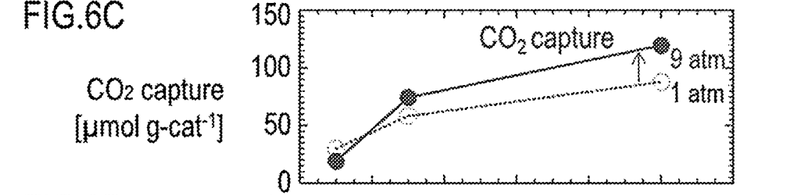
FIG. 6C shows the amount of $CO_2$ absorbed.
Figure 6D:
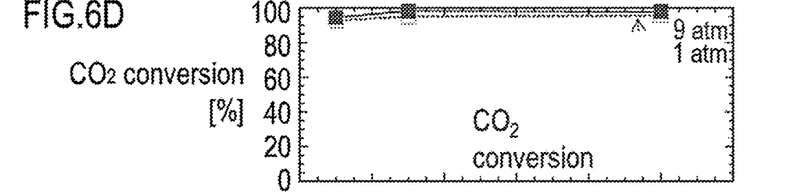
FIG. 6D shows the $O_2$ conversion rate.
Figure 6E:
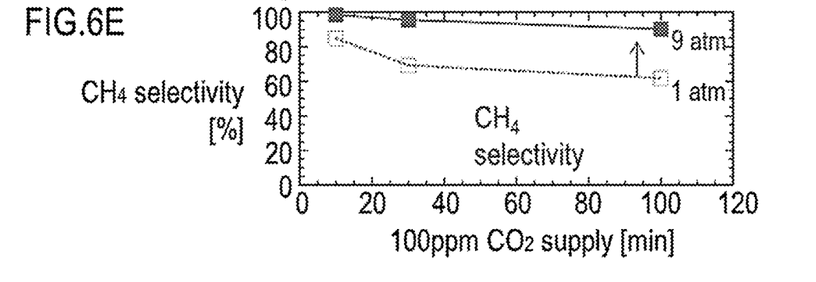
FIG. 6E shows the $CH_4$ selectivity.

As shown in FIGS. 6A and 6C, the amounts of the $CH_4$ formed and $CO_2$ captured using the $Ni/Na-Al_2O_3$ bifunctional catalyst increased corresponding to an increase in the $CO_2$ supply duration. In the case of 9 atm, in particular, an increase in the $CO_2$ uptake led to a larger increase, in the $CO_2$ supply duration until 100 minutes. These results suggest that pressurized conditions improve the $CO_2$ absorption and enable the $CO_2$ absorption for a longer period of time. As shown in FIG. 6D, the $CO_2$ conversion rate was higher than 90% in all reaction conditions using the $Ni/Na-Al_2O_3$ catalyst. However, as shown in FIG. 6E, the $CH_4$ selectivity was lower (from 60 to 85%) at 1 atm, and higher (from 90 to 98%) at 9 atm. Since the amount of $CO_2$ uptake and the $CH_4$ selectivity can be improved by applying a pressure, as described above, there is a possibility that the amount of catalyst required and/or the reactor size can be reduced.

As described above, it has been shown that it is possible to efficiently produce a hydrocarbon compound from $CO_2$ at concentrations including a low concentration range, by the production method of the Examples. In this production method, the absorption of $CO_2$ and the reaction with a reducing gas are performed at a pressure higher than the atmospheric pressure, using an absorption-conversion catalyst in which a $CO_2$ capture component such as an alkali metal or an alkaline earth metal, and a hydrocarbonation catalyst component such as Ni, Fe, Co, Cu or Ru, are supported on an oxide support.

As shown in (Experiment 5) to (Experiment 7) in Table 1, it was possible to produce a hydrocarbon compound even in the case of varying the concentration of the supplied $CO_2$ from a high concentration to an extremely low concentration, namely, from 5%, to 0.03% (300 ppm), and then to 0.01% (100 ppm). The 5% $CO_2$ concentration in this case is a high $CO_2$ concentration of 5% or more assuming that discharged from a thermal power plant or the like. Further, 0.03% is a low $CO_2$ concentration assuming that in the atmosphere, and 0.01% is an extremely low $CO_2$ concentration assuming a further lower concentration. As described above, it is possible to directly capture an extremely low to high concentration of $CO_2$ and convert it to a hydrocarbon compound.

The invention as understood by the disclosure described above can be exemplified as follows.

[1] A method for producing a hydrocarbon compound from carbon dioxide, the method comprising the steps of:
(a) providing an absorption-conversion catalyst comprising:
an oxide support;
a first component supported on the oxide support and comprising at least one selected from the group consisting of an alkali metal and an alkaline earth metal; and
a second component supported on the oxide support and comprising at least one selected from the group consisting of Ni, Fe, Co, Cu and Ru;
(b) bringing the absorption-conversion catalyst into contact with a gas containing carbon dioxide at a pressure higher than an atmospheric pressure, to allow the absorption-conversion catalyst to capture carbon dioxide; and
(c) bringing the absorption-conversion catalyst in which carbon dioxide is captured into contact with a reducing gas at a pressure higher than an atmospheric pressure, to obtain a hydrocarbon compound.

[2] The method according to [1], wherein the pressure in the steps (b) and (c) is more than 1 atm and not more than 9 atm.

[3] The method according to [1] or [2], wherein a concentration of carbon dioxide in the gas containing carbon dioxide in the step (b) is from 0.01 to 5%.

[4] The method according to any one of [1] to [3], wherein the first component in the step (a) comprises at least one selected from the group consisting of Na, Ca and K.

[5] The method according to [4], wherein the first component in the step (a) comprises Na.

[6] The method according to any one of [1] to [5], wherein the second component in the step (a) comprises Ni.

[7] The method according to any one of [1] to [6], wherein the absorption-conversion catalyst in the step (a) has an average particle size of from 0.1 to 500 μm.

[8] The method according to any one of [1] to [7], wherein the oxide support in the step (a) comprises an alumina support.

[9] The method according to any one of [1] to [8], wherein the reducing gas in the step (c) is a hydrogen-containing gas.

[10] The method according to any one of [1] to [9], wherein the hydrocarbon compound in the step (c) comprises at least one selected from the group consisting of hydrocarbons having carbon number of 1 to 5.

[11] The method according to any one of [1] to [10], wherein the hydrocarbon compound in the step (c) comprises at least one selected from the group consisting of methane and ethane.

[12] The method according to any one of [1] to [11], wherein carbon monoxide is obtained along with the hydrocarbon compound, in step (c).

[13] An apparatus for carrying out the method according to any one of [1] to [12], wherein the apparatus is a circulating fluidized bed type reactor, comprising:
a carbon dioxide capture reactor,
a hydrocarbon compound synthesis reactor, and
a catalyst circulation path connecting the carbon dioxide capture reactor and the hydrocarbon compound synthesis reactor.

INDUSTRIAL APPLICABILITY

The present invention can be expected to be used for the carbon recycling of $CO_2$ discharged from power plants, factories and the like, as well as the removal of $CO_2$ from the atmosphere, and the like.

The invention claimed is:

1. A method for producing a hydrocarbon compound from carbon dioxide, the method comprising the steps of:
   (a) providing an absorption-conversion catalyst comprising:
      an oxide support;
      a first component supported on the oxide support and comprising at least one selected from the group consisting of an alkali metal and an alkaline earth metal; and
      a second component supported on the oxide support and comprising at least one selected from the group consisting of Ni, Fe, Co, Cu and Ru;
   (b) bringing the absorption-conversion catalyst into contact with a gas containing carbon dioxide at a pressure higher than an atmospheric pressure, to allow the absorption-conversion catalyst to capture carbon dioxide; and
   (c) bringing the absorption-conversion catalyst in which carbon dioxide is captured into contact with a reducing gas at a pressure higher than an atmospheric pressure, to obtain a hydrocarbon compound.

2. The method according to claim 1, wherein the pressure in the steps (b) and (c) is more than 1 atm and not more than 9 atm.

3. The method according to claim 1, wherein a concentration of carbon dioxide in the gas containing carbon dioxide in the step (b) is from 0.01 to 5%.

4. The method according to claim 1, wherein the first component in the step (a) comprises at least one selected from the group consisting of Na, Ca and K.

5. The method according to claim 4, wherein the first component in the step (a) comprises Na.

6. The method according to claim 1, wherein the second component in the step (a) comprises Ni.

7. The method according to claim 1, wherein the absorption-conversion catalyst in the step (a) has an average particle size of from 0.1 to 500 μm.

8. The method according to claim 1, wherein the oxide support in the step (a) comprises an alumina support.

9. The method according to claim 1, wherein the reducing gas in the step (c) is a hydrogen-containing gas.

10. The method according to claim 1, wherein the hydrocarbon compound in the step (c) comprises at least one selected from the group consisting of hydrocarbons having carbon number of 1 to 5.

11. The method according to claim 1, wherein the hydrocarbon compound in the step (c) comprises at least one selected from the group consisting of methane and ethane.

12. The method according to claim 1, wherein carbon monoxide is obtained along with the hydrocarbon compound, in step (c).

* * * * *